(12) United States Patent
McChesney et al.

(10) Patent No.: US 6,376,511 B2
(45) Date of Patent: *Apr. 23, 2002

(54) 8-AMINOQUINOLINES

(75) Inventors: James McChesney, Boulder, CO (US); Dhammika N. Nanayakkara, Oxford, MS (US); Marilyn Bartlett, Indianapolis, IN (US); Arba L. Ager, Miami, FL (US)

(73) Assignee: The University of Mississippi, University, MS (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/155,509

(22) PCT Filed: Mar. 28, 1997

(86) PCT No.: PCT/US97/05160

§ 371 Date: Jun. 15, 1999

§ 102(e) Date: Jun. 15, 1999

(87) PCT Pub. No.: WO97/36590

PCT Pub. Date: Oct. 9, 1997

(51) Int. Cl.⁷ .................. A61K 31/47; C07D 215/40; A61P 33/02

(52) U.S. Cl. ............... 514/311; 514/312; 546/157; 546/171

(58) Field of Search ................. 514/311, 312; 546/171, 157

(56) References Cited

U.S. PATENT DOCUMENTS

| | | | | |
|---|---|---|---|---|
| 4,209,519 A | * | 6/1980 | Kinnamon | 424/258 |
| 4,431,807 A | * | 2/1984 | Strube | 546/171 |
| 4,554,279 A | * | 11/1985 | Saggiomo | 514/311 |
| 4,617,394 A | * | 10/1986 | Blumbergs | 546/157 |
| 4,980,360 A | * | 12/1990 | Nordiff | 514/311 |

OTHER PUBLICATIONS

Queener SF et al. Animicrob. Agents Chemother. 37, 2166–2172, 1993.*

Chen EH et al. J. Med. Chem. 30, 1193–99, 1987.*

* cited by examiner

*Primary Examiner*—Evelyn Mei Huang
(74) *Attorney, Agent, or Firm*—Greenberg Traurig, LLP; Eugene Rzucidlo, LLP

(57) ABSTRACT

It has been found that one of the enantiomers of 8-aminoquinoline antiparasitic compounds is surprisingly more active than the other enantiomer against parasitic infections including opportunistic parasitic infections. These enantiomers as well as pharmaceutical compositions containing pure enantiomers are disclosed. Also disclosed is a novel class of 8-aminoquinolines which contain a trisubstituted phenoxy substitution.

2 Claims, No Drawings

8-AMINOQUINOLINES

GRANT SUPPORT

This invention was supported by Public Health Service Grant #1 U01 AI35203 for the National Cooperative Drug Discovery Group.

This application is the National Phase of PCT/US97/05160 filed on Mar. 28, 1997.

FIELD OF INVENTION

The present invention relates to new compositions useful in treating parasitic and opportunistic infections. Additionally, the present invention relates to the use of enantiomers of 8-aminoquinoline compounds for the treatment of *Pneumocystis carinii*, pneumonia (PCP), toxoplasmosis, malaria, trypanosomaiasis, and leishmaniasis in mammals and the prevention of PCP and malaria in mammals.

BACKGROUND OF THE INVENTION

Parasitic diseases are a major health problem in the world. Malaria, due to one of four Plasmodium species, is the most widespread parasitic disease, with a reported total of 100 million clinical cases that lead to more than 1 million deaths annually. Trypanosomiases are diseases caused by the protozoa of the genus Trypanosoma. Two major forms of this disease occur in man: African trypanosomiasis (sleeping sickness) and American trypanosomiasis (Chagas disease). Some 16-18 million people are infected with *T. cruzi*, the cause of American trypanosomiasis, and it is estimated that 50 million people in some 36 countries are at risk of contracting African sleeping sickness [Ann. Trop. Med. Parasitol. 85, 43 (1991) M. L. Ruiz et al.]. Leishmaniases are a group of human parasitic diseases caused by protozoa of the genus Leishmania and are manifested in three major forms: cutaneous, mucocutaneous, and visceral. Visceral leishmaniasis, due mainly to *Leishmania donovani*, is fatal if untreated. Current therapies for this and the other parasitic diseases suffer significant shortcomings.

In addition to the significant morbidity and mortality associated with the parasitic infections, with the advent of AIDS epidemic, opportunistic parasitic diseases such as *Pneumocystis carinii* pneumonia, toxoplasmosis and cryptosporidiosis have become the leading cause of death among AIDS patients throughout the world. The non-availability of safe and efficacious drugs and drug resistance have hampered the effective treatment of all of these diseases.

Primaquine is an 8-aminoquinoline and the drug of choice for the radical cure of relapsing malaria [Drugs, 39, 160 (1990) D. M. Panisko et al. ibid 39, 337(1990) J. S Keystone] caused by *Plasmodium vivax* and *P. ovale* and is also being used as a prophylactic against all major forms of human malaria [Am. J. Trop. Med. Hyg. (supp), 49(3), Abrs. 417(1990) J. K. Baird et al.]. This drug was found to have significant sporontocidal and gametocytocidal [Military Med., 134, 802–819(1969) K. H. Rieckmann et al.] activity but very low activity against blood stage malaria parasites at therapeutic doses [Prog. Med. Chem., 28, 1(1991) E. A. Nodiff et al.]. Moreover, primaquine is reported to be active in animal models of other parasitic infections, including Trypanosomiasis [PQ Activity vs. Trypanosoma, J. Parasit., 74, 748 (1988) R. E. McCabe]. In addition to its activity against the parasitic infections, primaquine in combination with clindamycin has been successfully used for the treatment as well as prophylaxis of *Pneumocystis carinii* pneumonia in AIDS patients [South. Med. J., 83, 403(1990) R. Kay et al.; Lancet i, 1046(1989) E. Toma et al.; Clin. Infect. Dis., 14: 183(1992) G. S. Noskinm et al.]. This drug has also shown significant activity against other disease causing parasites such as Trypanosoma [J. Parasit., 74, 748(1988) R. E. McCabe] and Leishmanic [Am. J. Trop. Med. Hyg., 32, 753(1983) D. J. Berman et al.]. D. J. Berman et al.]. There are three reports on the use of primaquine for the treatment of *Trypanosoma cruzi* infection in humans [J. Parasit., 74, 748(1988) R. E. McCabe]. The major limitation of primaquine and other 8-aminoquinoline antimalarials is that they cause methemoglobinemia [N. Engl. J. Med., 279, 1127(1968) R. J. Cohen et al.] and hemolysis [Arch. Intern. Med. 109, 209(1962) A. R. Tarlov et al.] in individuals who suffer from glucose-6-phosphate dehydrogenase deficiency.

Over the years, several attempts have been made to improve the therapeutic index of primaquine against malaria and Leishmania through modification of its chemical structure. Introduction of 4-methyl and 5-phenoxy [J. Med. Chem. 25, 1094(1982) M. P. LaMontagne et al.; ibid, 25, 1097(1982) E. A. Nodiff et al.] or alkoxy groups [J. Med. Chem. 30, 1193(1987) E. H. Chen et al.] have produced analogs with much superior tissue and blood schizonticidal activity. However, toxicity studies have shown that these analogs also have a greater potential of producing methemoglobin [Fundam. Appl. Toxicol., 10, 270(1988) J. Anders et al.]. Recently, LaMontagne [J. Med. Chem., 32, 1728(1989) M. P. LaMontagne et al.] has reported that introduction of a methoxyl at position 2 of the quinoline ring reduces the toxicity of some of these compounds, especially induction of methemoglobin, without losing activity. Based on these results, the US Army selected an 8-aminoquinoline derivative, WR-238,605, as a potential replacement for primaquine for the treatment of relapsing malaria [Pharm. Res., 8, 1505(1991) R. P. Brueckner at el.].

Similarly, the US Army had selected WR-6026, a 4-methylprimaquine analog, as a potential drug for the treatment of leishmaniasis [Xenobiotica, 20, 31(1990) L. A. Shipley et al.]. Since the compound WR-6026 was selected as the potential candidate for the treatment of leishmaniasis in 1978 [Am. J. Trop. Med. Hyg., 27, 751(1978) K. E. Kinnamon et al.], a large number of 5-phenoxy or 5-alkoxy-4-methylprimaquine analogs have been synthesized. Some of these analogs have shown higher antileishmanial activity than WR-6026 in an in vitro assay [Am. J. Trop. Med. Hyg., 32, 753(1983) D. J. Berman et al.].

After the first report [*Antimicrob. Ag. Chemotherap.*, 32, 807(1988) S. F. Queener et al.] of antipneumocystis activity of primaquine in combination with clindamycin, several other 8-aminoquinolines were evaluated for antipneumocystic activity [Antimicrob. Ag. Chemotherap., 34: 277(1991) M. S. Bartlett et al.; ibid., 37, 2166(1993) S. Queener] and some of them, even when used alone, were found to be superior to the primaquine/clindamycin combination.

The effect of isomerism on biological activity and toxicity is well documented. However, this phenomenon has received little attention in the case of the 8-aminoquinolines. Schmidt et al [Antimicrob. Ag. Chemotherap., 12, 51 (1977) L. H. Schmidt] examined the relative curative and toxic activities of primaquine and its d- and l-_isomers in mice and rhesus monkeys. They confirmed an earlier report that d-primaquine was approximately 4 times as toxic as the l-form in mice but that the opposite is true in the rhesus monkey in which the l-form was 3 to 5 times as toxic as the d-primaquine and at least twice as toxic as, in which racemic primaquine. More importantly, all three forms of primaquine, the d- and l- and dl-, showed essentially identical curative properties against sporozoite induced *P. cynomolgi* infections. In studies on the metabolism of d- and l-isomers it was shown that the metabolic rates for the d- and l- isomers were different [J. Pharm. Sci., 77, 380(1988) J. K. Baker et al.]. Several other studies also have shown different activities and toxicities for d- and l-isomers [Biochem. Pharmacol., 37: 4605(1988) S. Agarwal et al.; FEBS Letts., 214, 291(1987) A. Brossi et al.]

The present invention relates to new and more active and/or less toxic compositions for the treatment of parasitic and opportunistic infections and diseases. These compositions comprise enantiomerically pure stereoisomers or mixtures of stereoisomers of 8-aminoquinoline analogs with the best activity and toxicity profile for the treatment and prevention of *Pneumocystis carinii* pneumonia (PCP), toxoplasmosis, malaria, trypanosomaiasis, and leishmaniasis in mammals.

SUMMARY OF INVENTION

The present invention relates to improvements in the chemotherapy of parasitic diseases through the separation of racemic 8-aminoquinoline compounds with desirable activity and toxicity profiles into pure enantiomers and the selection of the pure enantiomer with improved therapeutic and/or toxicity profile for enhanced treatment.

A number of compounds of the 8-aminoquinoline class were synthesized and their anti-parasitic activities were evaluated by administration of the test compounds to mice orally, in multiple doses. Compounds with optimum therapeutic and toxicity profiles were chosen, separated into enantiomers and the activity profile of the each enantiomer was determined. Surprisingly it was observed that (−) enantiomer of DN3-27-1 possessed significantly greater activity than the (+) enantiomer in the mouse model of PCP. It is speculated that the active enantiomer is responsible for the observed activity of DN3-27-1 at minimum effective doses. Hence, the present invention comprises the use of enantiomerically pure 8-aminoquinolines other than primaquine for the enhanced treatment of parasitic infections and diseases including opportunistic parasitic infections and diseases. The invention also encompasses new aminoquinolines which have not previously been described.

DETAILED DESCRIPTION OF THE INVENTION

In the experimental investigation leading to the present invention, the applicants prepared and evaluated the antipneumocystic, antitoxoplasma, antimalarial (blood schozontocidal activity), antitrypanosomal, and antileishmanial activities of 8-aminoquinoline analogs, which included some compounds, in their racemate form, that were previously reported to be active against malaria [J. Med. Chem., 25, 1094(1982) M. P. LaMontagne et al.; ibid, 25, 1097 (1982) E. A. Nodiff et al.; J. Med. Chem., 30, 1193(1987) E. H. Chen et al], and some novel analogs in their racemic form. Separation of the racemates provided enantiomerically pure isomers that were found to exhibit improved therapeutic and/or toxicity profiles.

The compounds in Table I have the following formulas:

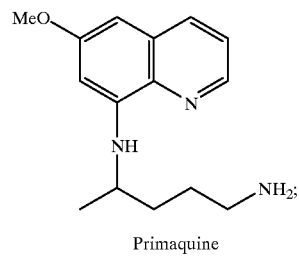

Primaquine

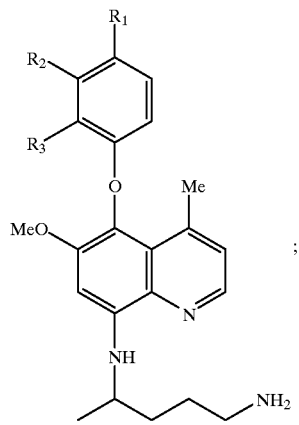

DN3-27-1: $R_1 = R_2 =$ Cl; $R_3 =$ H
1: $R_1 = R_3 =$ H; $R_2 =$ F
2: $R_1 = R_2 =$ F; $R_3 =$ H
3: $R_1 = R_3 =$ F; $R_2 =$ F

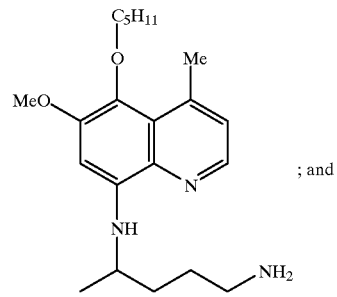

; and

4

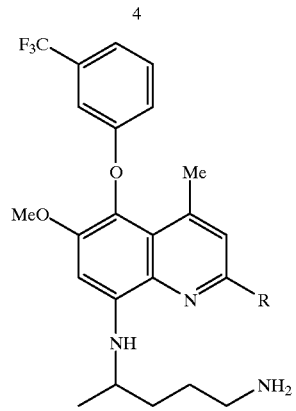

WR-238,605 R = OMe
WR-225,448 R = H

Antimalarial Activity

The blood schizonticidal activity of selected 8-aminoquinolines (Table I) was determined as described herein. Prophylactic efficacy of selected 8-aminoquinolines was determined as described herein.

TABLE I

Antimalarial Activity of 8-aminoquinolines: Blood schizontocidal activity against *P. berghei* in mice:
Mice surviving 60 days/Mice infected and treated

| | Oral Dose, mg/kg,day; (Total dose, mg/kg) | | | |
|---|---|---|---|---|
| | 1 (3) | 4 (12) | 16 (48) | 64 (192) |
| Compound # Primaquine | 0/7 | 0/7 | 1/7 | 3/7 |
| DN 3-27-1 | 7/7 | 7/7 | 7/7 | 7/7 |
| 1 | 4/7 | 7/7 | 7/7 | 1/7 |
| 2 | 6/7 | 7/7 | 7/7 | 5/7 |
| 3 | 2/7 | 7/7 | 7/7 | 6/7 |
| 4 | 7/7 | 7/7 | 4/7 | 0/7 |
| WR-225,448 | 7/7 | 7/7 | 7/7 | 4/7 |
| WR-238,605 | 0/7 | 1/7 | 7/7 | 1/7 |
| Control | 0/7 | | | |

DN3-27-1, is the most active and also the least toxic (no mice showed toxicity at the highest dose tested). This compound had also shown excellent activity by the subcutaneous route of administration [J. Med. Chem., 25, 1094 (1982) M. P. LaMontagne et al.] (See Table 2), and a higher radical curative activity (Table 3) than primaquine [J. Med. Chem., 25, 1094(1982) M. P. LaMontagne et al.].

TABLE 2

Suppressive Antimalarial Activity of DN3-27-1: Blood schizontocidal activity against *P. berghei* in mice (J. Med. Chem., 2 5, 1094(1982) M.P. LaMontagne et al.) Subcutaneously as a single dose
Mice infected and treated/Mice surviving 60 days

| | Dose, mg/kg | | | | | | | |
|---|---|---|---|---|---|---|---|---|
| Compound | 5 | 10 | 20 | 40 | 80 | 160 | 320 | 640 |
| DN3-27-1 | 5/4 | 5/5 | 5/5 | 5/5 | 5/5 | 5/5 | 5/5 | 5/5 |
| Control | 0/5 | | | | | | | |

Mice were treated with a single dose of the compound administered subcutaneously 72 h after infection. Number of cures is the number of mice surviving, out of five, 60 days postinfection.

TABLE 3

Radical Antimalarial Curative Activity of DN3-27-1 against *P. cynomolgi* in rhesus monkey (J. Med. Chem., 2 5, 1094(1982) M.P. LaMontagne et al.):
Orally multiple dose
Monkeys infected and treated/cured

| | Dose, mg/kg/day; (X7) | | |
|---|---|---|---|
| Compound | 0.1 | 0.316 | 1.0 |
| DN3-27-1 | 0/3 | 1/2 | 3/3 |
| Primaquine | | 0/2 | 1/2 |

Primaquine has been effectively used as a prophylactic against malaria. Several compounds were tested for oral prophylactic activity. Mice treated with a single dose of 2 mg/kg of compound DN3-27-1 within the period of 2 days preinfection through 2 days post infection were completely protected from malaria (Table 4).

TABLE 4

Prophylactic Activity of DN3-27-1.
Mice infected and Mice/treated surviving day 60

| | dose, mg/kg | | | |
|---|---|---|---|---|
| Day of Treatment | 2 | 8 | 32 | 128 |
| −3 | 0/5 | 5/5 | 5/5 | 5/5 |
| −2 | 5/5 | 5/5 | 5/5 | 5/5 |
| −1 | 5/5 | 5/5 | 5/5 | 5/5 |
| 1 | 5/5 | 5/5 | 5/5 | 5/5 |
| 2 | 5/5 | 5/5 | 5/5 | 5/5 |

TABLE 5

Prophylactic Anti-Malarial Activity of Enantiomers of DN3-27-1 (single dose of 2 mg/kg)

| Compound | Day of Treatment | Mice surviving day 60/Mice infected and treated |
|---|---|---|
| DN3-27-1 | −5 | 0/5 |
| X Enantiomer | −5 | 0/5 |
| Y Enantiomer | −5 | 0/5 |
| DN3-27-1 | −4 | 0/5 |
| X Enantiomer | −4 | 0/5 |
| Y Enantiomer | −4 | 0/5 |
| DN3-27-1 | −3 | 0/5 |
| X Enantiomer | −3 | 0/5 |
| Y Enantiomer | −3 | 0/5 |
| DN3-27-1 | −2 | 0/5 |
| X Enantiomer | −2 | 0/5 |
| Y Enantiomer | −2 | 1/5 |
| DN3-27-1 | 2 | 2/5 |
| X Enantiomer | 2 | 0/5 |
| Y Enantiomer | 2 | 5/5 |
| Controls | | 0/5 |

Antipneumocystis Activity

Primaquine in combination with clindamycin is currently being used for the treatment and as prophylaxis of *P. carinii* pneumonia in AIDS patients [South. Med. J., 83, 403(1990) R. Kay et al., Lancet i, 1046(1989) E. Toma e al., Clin. Infect. Dis., 14: 183(1992) G. S. Noskinm et al.]. Some of the 8-aminoquinolines, especially those bearing a 4-methyl and 5-phenoxy or alkoxy groups have shown superior in vivo antipneumocystis activity in mice compared to primaquine even when tested alone [Antimicrob. Ag. Chemotherap., 34: 277(1991) M. S. Bartlett et al., ibid., 37, 2166(1993) S Queener]. DN3-27-1 was evaluated for in vitro (Table 6) and in vivo (Table 7) antipneumocystis activity by the methods described hereinbelow.

TABLE 6

In vitro antipneumocystis activity of DN3-27-1

| Concentration (µg/ml) | % of control on day 7 |
|---|---|
| 10 | 3.2 |
| 1.0 | 40.5 |
| 0.1 | 76.7 |

TABLE 7

Oral antipneumocystis activity of DN3-27-1 in mice.
Number of animals with organism after treatment/Number of animals treated

| Compound | Dose: mg/kg/day (x21) | Giesma Stain | Silver Stain |
|---|---|---|---|
| DN3-27-1 | 1.2 | 1/10 | 1/10 |
| TMP/SMX | 50/250 | 1/10 | 1/10 |
| Control | | 10/10 | 10/10 |

Enantiomers of primaquine were prepared and evaluated for their antipneumocystis activity. One enantiomer showed significantly greater activity than the other.

TABLE 8

Oral anti-*Pneumocystis carinii* activity of primaquine in mice
Number of animals with organism after treatment/Number of animals treated

| Compound | Dose: mg/kg/day (x21) | Giesma Stain |
|---|---|---|
| Primaquine | 10 | 5/10 |
| (+) Enantiomer | 10 | 1/10 |
| (−) Enantiomer | 10 | 10/10 |
| Primaquine | 5 | 10/10 |
| (+) Enantiomer | 5 | 7/10 |
| (−) Enantiomer | 5 | 10/10 |
| Primaquine | 2 | 10/10 |
| (+) Enantiomer | 2 | 10/10 |
| (−) Enantiomer | 2 | 10/10 |
| TMP/SMX | 50/250 | 1/10 |
| Control | | 10/10 |

Antileishmanial Activity

DN3-27-1 has shown in vitro activity at very low concentrations against a variety of strains of Leishmania.

TABLE 9

In Vitro Anti-Leishmania Activity of DN-3-27-1

| Compound | Organism | Giesma Counts |
|---|---|---|
| None (Control) | *L. mexicana amazonensis* | 15.10 ± 2.18 |
| DN-3-27-1 10 μg/mL | *L. mexicana amazonensis* | 1.30 ± 0.38 |
| None (Control) | *L. donovani* Chagasi PP75 | 6.35 ± 068 |
| DN-3-27-1 50 ng/mL | *L. donovani* Chagasi PP75 | 0.95 ± 0.27 |
| DN-3-27-1 150 ng/mL | *L. donovani* Chagasi PP75 | 0.10 ± 0.03 |
| DN-3-27-1 450 ng/mL | *L. donovani* Chagasi PP75 | 0.00 ± 0.00 |
| Atovaquone 1350/ng/mL | *L. donovani* Chagasi PP75 | 5.05 ± 0.21 |

Antitoxoplasma Activity

Preliminary evaluation of DN3-27-1 in vitro against Toxoplasma gondii showed that it had an activity at around 50 μM.

Antitrypanisonal Activity: Table 10

Compounds were tested vs. trypanosome isolates grown as blood forms in HMI-18 (Hirumi H., Hirumi, K. 1989. Continuous Cuitivation of Trypanosoma brucei bloodstream forms in a medium containing a low concentration of serum portein without feeder cell layers. J. Parasitol. 75:985-989) containing 20% horse serum. Hemocytometer counts or Coulter counts were made daily and $IC_{50}$ values determined after 48 h.

| | $IC_{50}$ (μM) | | | |
|---|---|---|---|---|
| | EATRO Lab 110 | KETRI 243As103 | 243 | 269 |
| X | 8.3 | 36 | 34 | 37.0 |
| Y | 13.5 | 17.5 | 11 | 27.0 |
| DN3-27-1 | 9.4 | 10.9 | 29 | 5.0 |

The present invention, hence, relates to the finding that a particular enantiomer of DN3-27-1 as well as particular enantiomers of substituted 8-aminoquinolines other than primaquine have significantly greater activity and/or less toxicity than the other enantiomer or the diastereomeric mixture in the treatment of parasitic and opportunistic infections and diseases. The present invention relates to new 8-aminoquinoline compositions and to the pure active enantiomers of 8-aminoquinolines other than primaquine and also to the use of these compositions as pharmaceuticals when combined with an acceptable pharmaceutical carrier in the treatment of parasitic and opportunistic infections and diseases. The present compositions can also be used as prophylactics for the prevention of parasitic or opportunistic infections or diseases.

The antiparasitic activity of the compositions of the instant invention including the pure enantiomers and novel 8-amino-quinolines includes, for example, antimalarial activity and antipneumocystic activity. In each instance, the compositions would be employed using that amount of enantiomerically pure compound which is an effective amount to obtain the desired antiparasitic or antiinfective activity.

According to a specific embodiment the present invention, it is proposed to utilize compounds (+) 8-[(4-amino-1-methylbutyl)amino]-5-(3,4-dichlorophenoxy)-6-methoxy-4-methyl-quinoline (X) and (−) 8-[(4-amino-1-methylbutyl)amino]-5-(3,4-dichlorophenoxy)-6-methoxy-4-methyl-quinoline(Y) to treat *Pneumocystis carinii* pneumonia (PCP), toxoplasmosis, malaria, trypanosomiasis, or leishmaniasis.

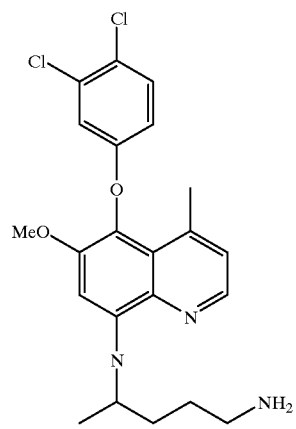

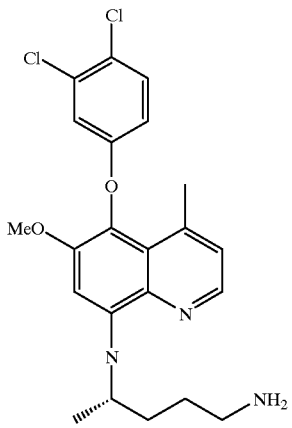

Administration of the compounds of the invention may be parenteral oral intravenous, intramuscular, subcutaneous, intrapleural, intrathecal, intraperitoneal, aerosol or transdermal administration to achieve the desirable antiparasitic effect. These drugs may be administered as the free base form or in the form of a pharmaceutically acceptable acid addition salt wherein the acid addition salt may be either organic or inorganic in nature. Suitable inorganic acids for salt formation include but are not restricted to: phosphoric acid, hydrochloric acid, sulfuric acid, or hydrobromic acid. Suitable organic acids for the formation of salts may include but are not restricted to: succinic acid, citric acid, fumaric acid, isothionic acid or pamoic acid. When administered orally, the compounds of the invention may be in the form of tablets (single or multilayer, coated or uncoated) capsules or dragees. These oral formulations may be admixed with a solid excipient such as lactose, sucrose, starch, microcrystalline cellulose, magnesium sterate, or talc. When parenteral administration may be indicated, an aqueous solution or an oleaginous formulation of the agent may be employed. Aqueous solutions can be prepared in water, physiological saline, Ringer's solution, or the like, either with or without buffers. Oleaginous formulation may be made in natural oils (as, peanut oil or olive oil), or in benzyl benzoate, for example.

The actual dosage amount administered can be determined by physical and physiological factors such as body weight, severity of condition, and idiopathy of the patient. With these considerations in mind, the dosage of an active 8-amino-quinoline for a particular subject and/or course of treatment can readily be determined.

Both enantiomers X and Y mentioned, hereinabove, are to be included as preferred antiparasitic agents and advantage may accrue in the choice of one or the other of these. The preferred salts include succinate, phosphate, and citrate.

The present invention relates to compounds of the formula:

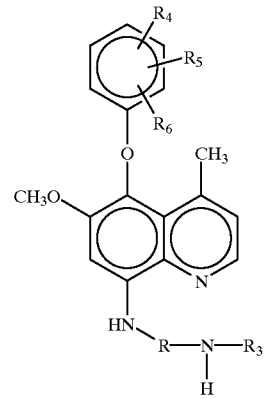

wherein R is an alkylene group which is

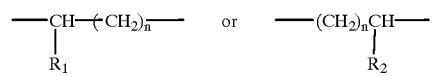

wherein n is 3 or 4, wherein $R_1$ and $R_2$ are methyl or ethyl; wherein $R_3$ is hydrogen or isopropyl, wherein $R_4$, $R_5$ and $R_6$ are hydrogen, chloro, bromo, fluoro, trifluoromethyl or methoxy groups, and wherein the compound is a free amine or a pharmaceutically acceptable acid amine salt.

Preferred compounds within this class of compounds include:

1. 8-((4-Amino-1-methylbutyl)amino)-6-methoxy-4-methyl-5-(2,4,5-trichlorophenoxy)-quinoline 2. 8-((4-Amino-1-pentyl)amino)-6-methoxy-4-methyl-5-(2,4,5 trichlorophenoxy)-quinoline 3. 8-((5-Amino-1-hexyl)amino)-6-methoxy-4-methyl-5-(2,4,5-trichlorophenoxy)-quinoline 4. 8-((4-Amino-1-ethylbutyl)amino)-6-methoxy-4-methyl-5-(2,4,5-trichlorophenoxy)-quinoline 5. 8-((4-Isopropylamino-1-methylbutyl)amino)-6-methoxy-4-methyl-5-(2,4,6;tritrifluoromethylphenoxy)-quinoline 6. 8-((4-Amino-1-methylbutyl)amino)-6-methoxy-5-(2,4,6-trichlorophenoxy)-4-methyl-quinoline 7. 8-((4-Amino-1-methylbutyl)amino)-2,4,5-trifluorophenoxy)-6-methoxy-4-methylquinoline 8. 8-((4-Amino-1-methylbutyl)amino)-5-(2,4,5-tritrifluoromethylphenoxy)-6-methoxy-4-methylquinoline The present invention further relates to enantiomerically pure 8-aminoquinoline compounds such as DN3-27-1, WR-238,605, WR-225-448 and compound 4 shown on hereinabove. The enantiomeric compounds encompassed by the invention in each instance is that enantiomer which provides significantly greater activity than the other enantiomer and/or lesser toxicity than the other. Enantiomeric separation is within the skill in the art. A preferred method in the instant invention is derivatization with (R)(+)-α-methylbenzyl isocyanate and separation using C-18 reverse-phase column chromatography or fractional crystallization. Another preferred method in the instant invention is derivatization with S(−)-α-methylbenzyl isocyanate and separation using C-18 reverse-phase column chromatography of fractional crystallization.

A general reaction scheme for the preparation of compounds with the scope of the present invention as well as enantiomerically pure compounds is as follows:

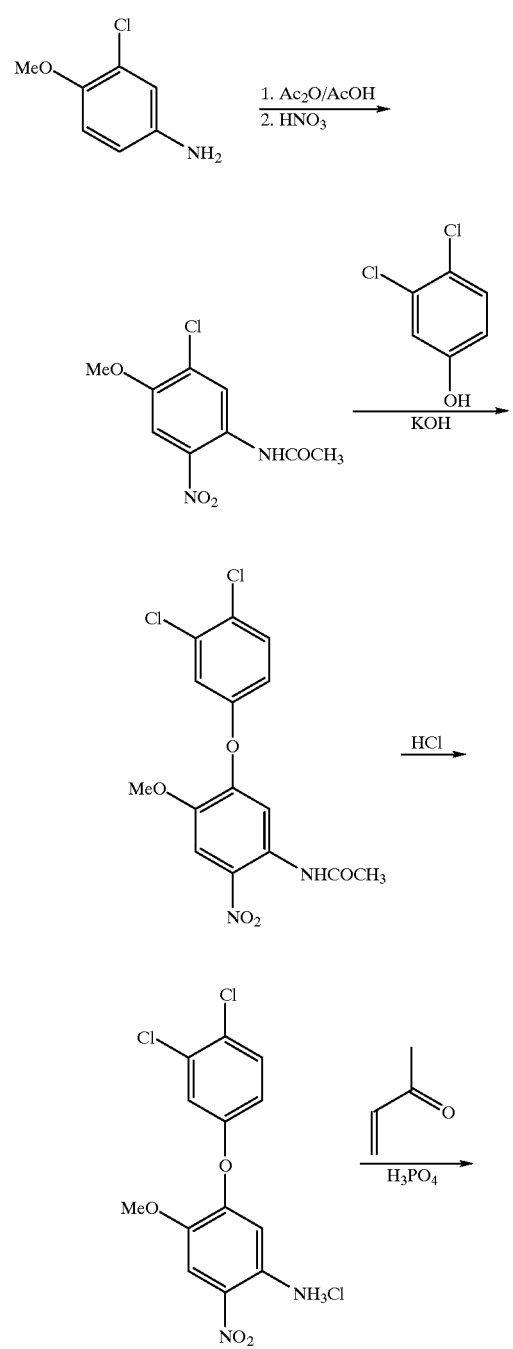
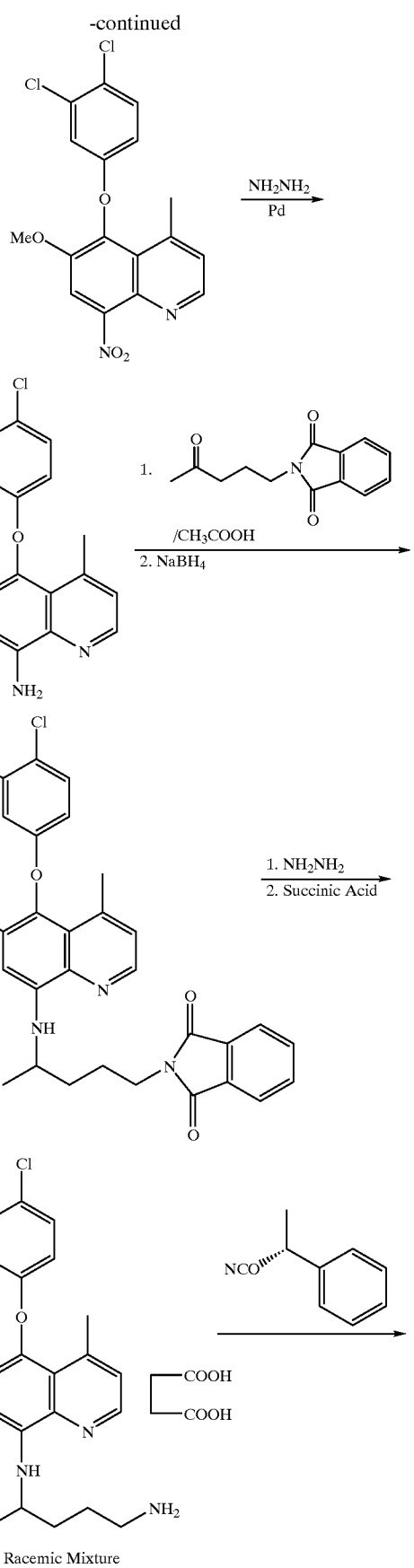

Racemic Mixture

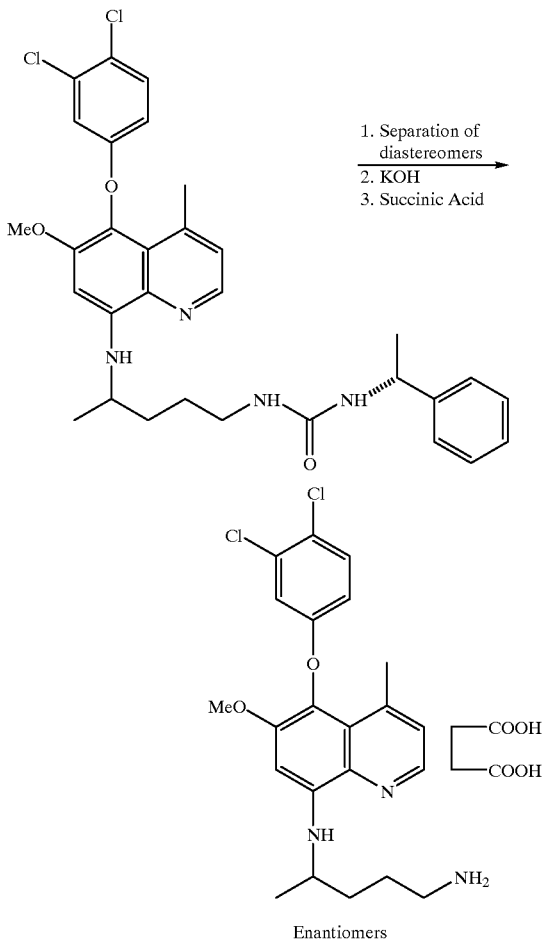

Enantiomers

In order to further illustrate the present invention and the advantages thereof, the following specific examples are given, it being understood that the same is intended only as illustrative and in no way limitative.

In the examples below as well as elsewhere in this specification, all temperatures are in degrees Celsius (° C.).

Reactions for the preparation of DN3-27-1 and compounds X and Y

2-Nitro-4-methoxy-5-(3,4-dichlorophenoxy)acetanilide

A solution of 50 g of 3,4-dichlorophenol (0.307 mole) and 20.2 g of 85% KOH (0.307 mole) in 250 ml of dry DMF was added into a 67.6 g solution of 2-nitro-4-methoxy-5chloroacetanilide (0.275 mole) in 250 ml of DMF at 120° C. with stirring under nitrogen atmosphere. After the addition was complete the reaction mixture was stirred for further 5 hours at this temperature. The reaction mixture was poured into cold water with stirring. The resulting precipitate was separated by filtration and was crystallized from chloroform/methanol to yield 84 g of the product, 2-nitro-4-methoxy-5-(3,4-dichlorophenoxy)acetanilide 2-Nitro-4-methoxy-5-(3,4-dichlorophenoxy)aniline hydrochloride A mixture of 84 g of 2-nitro-4-methoxy-5-(3,4-dichlorophenoxy)acetanilide (0.22 mole) and 100 ml of concentrated HCl in 1l of ethanol was refluxed for 5 hours. The solvent was removed under vacuum and the product obtained was used in the next reaction without further purification.

5-(3,4-Dichlorophenoxy)-6-methoxy-4-methyl-8-nitroquinoline

A mixture of 83 g of 2-nitro-4-methoxy-5-(3,4-dichlorophenoxy)aniline hydrochloride (0.22 mole) polyphosphoric acid in 250 ml of 85% phosphoric acid was heated in a nitrogen atmosphere at 110–120° C. and 32.17 g of methyl vinyl ketone (0.46 mole) was added dropwise under vigorous stirring. After the addition was complete, the mixture was stirred and maintained at 110–120° C. for a further 4 hours. An additional 14 g of methyl vinyl ketone (0.2 mole) was added and the mixture was heated for a further 4 hours. The reaction mixture was poured into ice cold sodium hydroxide solution (pH 10–12) and left over night. The resulting precipitate was separated by filtration and dried. The solid was dissolved in chloroform and mixed with activated charcoal and filtered through a celite bed. The celite bed was washed with chloroform and the filtrate was concentrated to 400 ml under vacuum and diluted with methanol until a turbidity appeared and left overnight. The crystalline product formed was separated by decantation and crystallized from chloroform to give 8 g of pure product, 5-(3,4-dichlorophenoxy)-6-methoxy-4-methyl-8-nitroquinoline. The combined filtrates were evaporated to dryness and the residue was chromatographed over silica gel with 30% chloroform in hexane to yield a fraction from which the product which was crystallized (chloroform/methanol) to give 13 g of product.

8-Amino-5-(3,4-dichlorophenoxy)-6-methoxy-4-methylquinoline

To a mixture of 13 g of 5-(3,4-dichlorophenoxy)-6-methoxy-4-methyl-8-nitroquinoline and 800 mg of 10% Pd on carbon in 500 ml of ethanol, was added 20 ml of 98% hydrazene hydrate portionwise with stirring. After the addition was complete, the reaction mixture was refluxed for 6 hours. The reaction mixture was filtered while hot and evaporated. The residue was partitioned between water and ethyl acetate, the organic layer was washed with water, dried and evaporated to give 12.4 g of crystalline product which was used in next reaction without further purification.

5-(3,4-dichlorophenoxy)-6-methoxy-1methyl-8-[(4-phthalimido-1-methylbutyl)amino]quinoline A mixture of 12.4 g of 8-amino-5-(3,4-dichlorophenoxy)-6-methoxy-4-methylquinoline (36 mM) and 11.6 g of 4-oxo-1-phthalimidopentane (50 mM), in glacial acetic acid was stirred for 15 min under nitrogen and 2.6 g of sodium borohydride (70 mM) was added portionwise maintaining the temperature 25–35° C. After the addition, the reaction mixture was stirred for 30 min and then poured into ice cold solution of concentrated sodium hydroxide. The resulting precipitate was filtered and chromatographed over silica gel. Elution with hexanes:ethyl acetate 90:10 yielded the expected product of 5-(3,4-dichlorophenoxy)-6-methoxy-4-methyl-8-[(4-phthalimido-1-methylbutyl)amino]quino line which was crystallized from ether to give 12.4 g (22 mM) of yellow crystalline product.

8-[(4-amino-1-methylbutyl)amino]-5-(3,4-dichlorophenoxy)-6-methoxy-4-methylquinoline.

A mixture of 12.2 g of 5-(3,4-dichlorophenoxy)-6-methoxy-4-methyl-8-[(4-phthalimido-1methylbutyl)amino]quinoline (21.6 mM) and 4 ml of 98% hydrazene hydrate in 500 ml of ethanol was refluxed 5 hours. The reaction mixture was evaporated under vacuum and the residue was partitioned between 400 ml of 10% potassium hydroxide and 400 ml of ethyl acetate. The organic layer was washed twice with 300 ml of 10% potassium hydroxide then four times with water, dried with anhydrous sodium sulfate and evaporated. The residue was used in the next reaction with out further purification.

8-[{4-(N(R)-1-phenylethylcarbamoyl)-1-methylbutyl}amino]-5-(3,4-dichlorophenoxy)-6methoxy-4-methyl-quinoline To a stirred solution of 8 g (18.4 mM) of 8-[(4-amino-1-methylbutyl)amino]-5-(3,4dichlorophenoxy)-6-methoxy-4-methyl-quinoline in toluene at 10° C., 2.98 g (20.3 mM )of (R)(+)-α-methylbenzyl isocyanate was added dropwise. The mixture was stirred for 30 mins and then the solvent was evaporated in vacuum and the residue was boiled in 200 ml of ethyl acetate and filtered. The ethyl acetate in soluble fraction was crystallized twice from ethyl acetate to give one diastereoisomer (I) in pure form 1.2 g.

Ethyl acetate soluble fraction was recrystallized four times from methanol to give other diastereoisomer (I) in pure form (420 mg).

(−)-8-[(4-amino-1-methylbutyl)amino]-5-(3,4-dichlorophenoxy)-6-methoxy-4-methylquinoline succinate (Y)

A mixture of 800 mg of diastereomer I of 8-[{4-(N(R)-1-phenylethylcabamoyl)-1-methylbutyl}amino]-5-(3,4-dichlorophenoxy)-6-methoxy-4-methyl-quinoline and 8 gm of 85% potassium hydroxide in 80 ml of n-butanol was refluxed under nitrogen for 30 hours. The solvent was evaporated under vacuum and the residue was partitioned between ethyl acetate and water. The ethyl acetate layer was separated and the aqueous layer was extracted with ethyl acetate. The combined ethyl acetate layers were washed four times with water, dried over anhydrous sodium sulfate and evaporated. The gum obtained was chromatographed over basic alumina and elusion with ethyl acetate:methanol yielded 462 mg of 8-[(4-amino-1-methylbutyl)amino]-5-(3, 4-dichlorophenoxy)-6-methoxy-4-methylquinoline (1.06 mM). This was dissolved in 10 ml of ethanol containing 126 mg of succinic acid, diluted with 30 ml of diethyl ether and left overnight at 4° C. The resulting solid was separated by filtration to yield 373 mg of (−) 8-[(4-amino-1-methylbutyl) amino]-5-(3,4-dichlorophenoxy)-6-methoxy-4-methyl-quinoline succinate.

(+) 8-[(4-amino-1-methylbutyl)amino]-5-(3,4-dichlorophenoxy)-6-methoxy-4-methylquinoline succinate (X)

A mixture of 285 mg of diastereomer II of 8-[{4-(N(R)-1-phenylethylcabamoyl)-1-methylbuty}amino]-5-(3,4-dichlorophenoxy)-6-methoxy-4-methyl-quinoline and 3 gm of 85% potassium hydroxide in 30 ml of n-butanol was refluxed under nitrogen for 30 hours. The solvent was evaporated under vacuum and the residue was partitioned between ethyl acetate and water. The ethyl acetate layer was separated and the aqueous layer was extracted with ethyl acetate. The combined ethyl acetate layers were washed four times with water dried over anhydrous sodium sulfate and evaporated. The gum obtained was chromatographed over basic alumina and elusion with ethyl acetate:methanol yielded 157 mg (0.36 mM) of 8-[(4-amino-1-methylbutyl)amino]-5-(3,4-dichlorophenoxy)-6-methoxy-4-methyl-quinoline. This was dissolved in 10 ml of ethanol containing 43 mg (0.36 mM) of succinic acid, diluted with 30 ml of diethyl ether and left overnight at 4° C. The resulting solid was separated by filtration to give 158 mg of (+) 8-[(4-amino-1-methylbutyl)amino]-5(3,4-dichlorophenoxy)-6-methoxy-4-methyl-quinoline succinate. Diastereomers obtained after the derivatization with (R)(+)-α-methylbenzyl isocyanate were also separated using C-18 reverse-phase column chromatography. This HPLC analysis method and proton NMR spectroscopy were used to determine the purity of the diastereomers.

HPLC Analysis. Instrumentation consisted of a Waters LC Module I Multisolvent Delivery System, Waters 715 autoinjector, Waters pump 600, Waters UV detector 486 operating at 254 nm (Millipore Corporation, Waters Chromatography Division, Milford, Mass.) and a computer (NEC power mate 386/33i, Millennium 2000) for control of the analytical system, data collection and processing.

Chromatography was carried out using Waters Resolve® (5μ spherical, 3.9×30 mm) C- 18 reverse-phase column and acetonitrile:tetrahydrofuran:85% lactic acid (76.5:13.5:10) mobile phase at a flow rate 2 ml./min. Compounds were detected using an UV detector operating at 254 nm.

(+) and (−) Primaquine

Primaquine was purchased from Aldrich Chemical Co. (Milwaukee, Wis.) and separated into (+) and (−) enantiomers using the procedure described by Carroll et al.[J. Med Chem., 21, 326 (1978), F. I. Carroll et al.].

BIOLOGICAL TESTING PROCEDURES IN ANIMALS

Blood Schizontocidal Test (Trophozoite-Induced *Plasmodium berghei* Infection in mice University of Miami, Test System: Thompson Test Drugs were mixed in 0.5% hydroxycellulose 0.1% Tween 80 and administered orally b.i.d. on days 3, 4 and 5 postinfection. CD-1 male or female mice, 5 weeks of age, were infected with $5 \times 10^4$ parasitized erythrocytes of *Plasmodium berghei* KBG-173 mm strain. Blood films were taken on day +6 and weekly thereafter until day +60. Parasitemias were calculated and SD90 value (dose suppressing 90% of the parasites in treated groups compared with the infected non-treated controls) on day +6 postinfection. Mortality data was tabulated for 60 days at which time all mice surviving that were blood film negative were considered cured.

Compounds X and Y were tested at three dose levels, 4, 1, and 0.25 mg/kg body weight per day. The activity of these compounds were compared with the untreated control and "racemate" which is a mixture of equal amount of each enantiomer X and Y. In untreated controls, death occurs within 8–9 days. Compounds which are effective against *Plasmodium berghei* infection increase the mean survival time of the infected animals when compared with the untreated controls. Mice that survive after thirty days and are free of parasites in blood are considered cured.

Efficacy of the drug is determined by the number of cures at the end of a 30 day period and the increase in mean survival time over the control (ΔMST). The effect of the test drugs also could be determined by the reduction of the parasitemia (percentage of the red blood cells detected with the parasites) over the untreated control on day 6, one day after the treatment is completed. Both these methods yield virtually identical results. If the dose of test compounds are inadequate, after initial clearance, residual parasites will multiply and relapses will occur within thirty days. The blood schizontocidal activities (suppressive antimalarial) of X, Y, and racemate against *P. berghei* in mice are shown in Table 11.

Prophylactic Test

Drugs were mixed in 0.5% hydroxycellulose 0.1% Tween 80 and administered orally b.i.d. either on day 5, 4, 3, 2, or 1 prior to the infection or 1 or 2 days postinfection. CD-I male or female mice, 5 weeks of age, were infected with $5 \times 10^4$ parasitized erythrocytes ot *Plasmodium berghei* KBG-173 mm strain. Blood films were taken on day +6 and weekly thereafter until day+30. Mortality data was tabulated for 30 days at which time all mice surviving that were blood film negative were considered cured. The prophylactic activities of X, Y, and racemate against *P. berghei* in mice are shown in Table 5.

Anti-*Pneumocystis carinii* Test (Induced *Pneumocystis carinii* Infection in Mice)

This test is designed to evaluate the effectiveness of test compounds for the treatment of *Pneumocystis carinii* pneumonia in immunosuppressed animals.

Virus and *Pneumocystis carinii*-free mice were utilized. Animals received standard chow containing 23% protein and also received tetracycline (0.5 mg/mL) in the drinking water.

Animals were immunosuppressed with dexamethasone at 1.2 mg/kg or 4.8 mg/kg in drinking water and 7–14 day animals were transtracheally inoculated with *P. carinii* and were continued on immunosuppressive agents. For transtracheal inoculation, animals were anesthetized intramuscularly with 0.02 mL of a ketamine cocktail containing ketamine hydrochloride (80.0 mg/mL), atropine (0.38 mg/mL), and acepromazine (1.76 mg/mL), and an incision of approximately 1 cm was made over trachea, which was then exposed by blunt dissection. The inoculum of $10^6$ organisms in 0.05 mL and 0.4 mL of air were injected sequentially. The wound was closed with a single clip. The animals were continued on immunosuppressive agents. At 3 weeks post inoculation, treatment was begun and continued for three weeks. Compounds X and Y were tested at 4 dose levels, 5, 1, 0.5 and 0.25 milligram per kilogram body weight per day. ARacemate@ which is a mixture of equal amount of each enantiomer X and Y was tested at dose levels 1.3 and 0.25 mg/kg/day. A group of untreated animals served as a control and a group of trimethoprim (TMP)/sulfamethoxazole (SMX)-treated (50/250 mg/kg/day) animals served as a positive treatment control. At the end of three weeks of therapy, animals were anesthetized and exsanguinated by cardiac puncture. Lungs were removed and representative portions were used to make impression smears. Four impression smears, fixed in methanol, were evaluated for the presence of *P. carinii* by staining with Giemsa and modified methanamine silver nitrate. Slides were blinded and reviewed microscopically by three examiners who scored them on the following basis: More than 100 organism per x1,000 field, 5+; 11–100 organisms per field 4+; 1–10 per field 3+; 2–9 in ten field 2+; 1 in 10 or more fields 1+; no organism in 50 fields 0. Means of these scores were separately determined for the Giemsa-stained and silver-stained impression smears. Giemsa stains reveal living trophozoite forms and cyst forms. Silver stains reveal both living and dead cyst forms. For this reason Giemsa stains provide more reliable results and silver stains data were used to confirm the conclusions. The anti-*Pneumocystis carinii* pneumonia activity of X, Y, and racemate against Pneumocystis in mice is shown in Table 12.

Biological Activity

Antimalarial Activity Test Data

TABLE 11

Suppressive Antimalarial Activity of X, Y and Racemate Against *P. berghei* in mice

| Compound | mg/kg/ day | mg/kg Total | ΔMST days | Mice Alive Day 26 | Parasitemia Day 6 |
|---|---|---|---|---|---|
| X | 4 | 12 | 11 | 0/5 | 1.1 |
|  | 1 | 3 | 6 | 0/5 | 27.4 |
|  | 0.25 | 0.75 | 0 | 0/5 | 28.2 |
| Y | 4 | 12 |  | 5/5 | 0.0 |
|  | 1 | 3 | 13.6 | 4/5 | 0.0 |
|  | 0.25 | 0.75 | 11.6 | 0/0 | 0.2 |
| Racemate | 1 | 3 | 10.2 | 0/5 | 0.1 |
|  | 0.25 | 0.75 | 11.6 | 0/5 | 4.8 |
| Control | 0 | 0 | 0 | 0/5 | 31.8 |

ΔMST = increase in mean survival time over the control

TABLE 12

Oral Anti-*Pneumocystis carinii* activity of X, Y and racemate in mice

| Compound | Dose: mg/kg/ day (x21) | Giemsa Stain I/T | Score | Silver stain I/T | Score |
|---|---|---|---|---|---|
| X | 5 | 0/10 | 0.0 | 0/10 | 0.0 |
| Y | 5 | 0/10 | 0.0 | 0/10 | 0.0 |
| Racemate | 1.3 | 0/10 | 0.0 | 0/10 | 0.0 |
| X | 1 | 0/10 | 0.0 | 0/10 | 0.0 |
| Y | 1 | 0/10 | 0.0 | 0/10 | 0.0 |
| X | 0.5 | 2/10 | 0.20 ± 0.10 | 2/10 | 0.1 ± 0.1 |
| Y | 0.5 |  |  |  |  |
| X | 0.25 | 6/10 | 0.55 ± 0.16 | 10/10 | 1.15 ± 0.16 |
| Y | 0.25 | 0/10 | 0.0 | 0/10 | 0.0 |
| Racemate | 0.25 | 2/10 |  |  |  |
| TMP/SMX | 50/250 | 1/10 | 0/03 ± 0.02 | 0/10 | 0.0 |
| Control |  | 10/10 | 4.43 ± 0.12 | 10/10 | 3.80 ± 0.08 |

I/T = Number of animals with organism after treatment/Number of animals treated
Anti-*Pneumocystis carinii* Test Data Unless defined otherwise, all technical and scientific terms used herein have the same meaning as commonly understood by one of ordinary skill in the art to which this invention belongs. Although any methods and materials similar or equivalent to those described can be used in the practice of testing of the present invention, the preferred methods and materials are now described. All publications and patent documents referenced in this application are incorporated herein by reference in their entirety as though each and every publication and patent document was specifically incorporated herein by reference in its entirety.

It is understood that the examples and embodiments described herein are for illustrative purposes only and the various modifications or changes in light thereof will be suggested to persons skilled in the art and are to be included within the spirit and purview of this application and scope of the appended claims.

We claim:

1. A composition for the prevention or treatment of *Pneumocystis carinii* pneumonia, toxoplasmosis, malaria, leishmaniasis, or trypsonosomia, the composition consisting of enantiomercially pure (−) 8[(4-amino-1-methylbutyl)amino]-5-(3,4- dichlorophenoxy)-6-methoxy-4-methyl-quinoline, and a pharmaceutically acceptable carrier.

2. A method of treating or preventing malarial, pneumocystic, toxoplasmic, leishmaniac, and trypanosomic infections, the method comprising administering to a subject in need of such prevention or treatment an effective amount of a composition consisting of enantiomerically pure (−) 8-[(4-amino-1-methylbutyl)amino]-5-(3,4-dichlorophenoxy)- 6-methoxy-4-methyl-quinoline and a pharmaceutically acceptable carrier.

* * * * *